(12) United States Patent
Farringdon et al.

(10) Patent No.: US 6,807,869 B2
(45) Date of Patent: Oct. 26, 2004

(54) SHOE BASED FORCE SENSOR AND EQUIPMENT FOR USE WITH THE SAME

(75) Inventors: Jonathan Farringdon, Pittsburgh, PA (US); Paul A. Gough, Smallfield (GB); Andrew J. Moore, Brighton (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 38 days.

(21) Appl. No.: 10/304,104

(22) Filed: Nov. 25, 2002

(65) Prior Publication Data

US 2003/0097878 A1 May 29, 2003

(30) Foreign Application Priority Data

Nov. 29, 2001 (GB) .............................................. 0128528

(51) Int. Cl.⁷ .................................................. G01L 3/00
(52) U.S. Cl. ................................................. 73/862.046
(58) Field of Search ......................... 73/172; 340/573.1

(56) References Cited

U.S. PATENT DOCUMENTS

| | | | | |
|---|---|---|---|---|
| 4,203,088 A | | 5/1980 | Sado et al. | 338/114 |
| 4,529,959 A | | 7/1985 | Ito et al. | 338/295 |
| 5,323,650 A | * | 6/1994 | Fullen et al. | 73/172 |
| 5,437,289 A | * | 8/1995 | Liverance et al. | 36/136 |
| 5,471,405 A | | 11/1995 | Marsh | 364/556 |
| 5,586,557 A | | 12/1996 | Nelson et al. | 128/779 |
| 5,813,142 A | * | 9/1998 | Demon | 73/172 |
| 5,941,835 A | * | 8/1999 | Sundman | 73/172 |
| 6,195,921 B1 | * | 3/2001 | Truong | 73/172 |

FOREIGN PATENT DOCUMENTS

| | | | |
|---|---|---|---|
| EP | 0415036 A2 | 6/1991 | A61B/5/107 |
| EP | 0989508 | 3/2000 | G06F/161/00 |
| WO | WO0072239 | 11/2000 | G06K/11/12 |

OTHER PUBLICATIONS

Partial English Translation of German–Language Patent Application EP 415,036 (Col. 4, line 40 to Col. 5, line 49).*

* cited by examiner

*Primary Examiner*—Edward Lefkowitz
*Assistant Examiner*—T Miller
(74) *Attorney, Agent, or Firm*—Aaron Waxler (57) ABSTRACT

A sensor for detecting the presence of a force exerted by a persons foot on the ground is provided in a shoe, the sensor interposed between the foot and the ground in the region of the sole of the shoe. The sensor includes a resilient compressible elastomeric middle layer of insulating material disposed between a lower conductive fabric layer and a plurality of upper conductive fabric layer portions. The resilient elastomeric layer includes a plurality of embedded electrically conductive metal filaments extending from a first surface towards a second surface of the elastomeric layer. In regions of the sensor compressed by force 'F' due to a persons weight the thickness of the elastomeric layer is reduced and so the metal filaments are of sufficient length to provide electrical continuity through the elastomeric layer between the lower and upper conductive fabric. The occurrence of such continuity is monitored and processed by a system to provide data for use in the field of sports training and athlete monitoring applications.

20 Claims, 5 Drawing Sheets

SHOE BASED FORCE SENSOR AND EQUIPMENT FOR USE WITH THE SAME

The present invention relates to a force sensor suitable for incorporation into a shoe for detecting application of a persons foot to a supporting surface and to apparatus suitable for receiving and processing signals received from such sensors. In particular the present invention relates to the use of such equipment for sports training and athlete monitoring applications.

A known in-shoe dynamic pressure measuring system is produced by Novel GmbH and marketed as the 'pedar' range. With reference to the Novel internet web site (http://www.novel.de/pedar.htm—viewed 31st Oct. 2001), the system is presented as one which includes in-shoe sensors in the form of in-soles with tails extending from each insole for establishing a wired connection with monitoring equipment. The intended applications of the system include gait analysis, rehabilitation assessment, shoe research and design, field testing of sport applications and long term load monitoring. An emphasis is placed on the ability to perform accurate and reliable pressure distribution measurement for monitoring of local loading of the foot inside the shoe. A computer aided calibration procedure allows all sensors of the pedar system to be calibrated individually by using a process employing homogeneous air pressure.

The pedar system is available as a package including analysis software and a number of insoles each having a plurality of sensors distributed over the insole area. The system would appear to be directed to the medical and research market and as such is of an arrangement and cost which make it less suited to mass market commercialisation in the field of sports training and athlete monitoring applications.

It is an object of the present invention to provide a sensor which may be located in a shoe and which is suitable for use in the field of sports training and athlete monitoring applications.

In accordance with a first aspect of the present invention there is provided a sensor for detecting the presence of a force exerted by a persons foot on a supporting surface, said sensor arranged to be interposed between the foot and the supporting surface and therefore subjected to the force, in response to which force the sensor exhibits a change in an electrical characteristic, said sensor comprising:

a resilient compressible material exhibiting a first surface and a second surface and at least partially accommodating one or more electrically conductive body shaped and orientated within the material such that when the compressible material is in an uncompressed state the separation of the first and, second surfaces is sufficient that the conductive body or bodies do not extend to span the first and second surface simultaneously, whereas when the sensor is subject to the force the compressible material adopts a compressed state having reduced separation between the first and second surfaces such that the conductive body or bodies extend to and span the first and second surfaces simultaneously; and contact portions adjacent each of the first and second surface for making electrical connection with the electrically conductive body or bodies when they extend to the or each first and second surface.

Therefore, in one arrangement the act of compressing the resilient compressible material, therefore reducing the separation between its first and second surface may allow one or more of the electrically conductive bodies to reach the first and second surface simultaneously. If this occurs, the or each electrically conductive body will provide a path of relatively low electrical resistance between the resilient compressible material first and second surface (in comparison with the condition when the electrically conductive bodies do not extend to span the first and second surface) and therefore between the first and second contact portions adjacent the first and second surface. Thus, the act of applying a force to compress the resilient compressible material brings about a change of electrical characteristic when measured at the contact portions, in particular a reduction in electrical resistance, to provide an electrical switching action. Removal of the compressive force allows the resilient material to return to its uncompressed state. In some cases the application of force bringing about compression may cause one or more electrically conductive body to protrude beyond the first or second surface.

One or more of the conductive bodies may consist of more than one part each arranged to unite and collectively extend to the first and second surface simultaneously when the material adopts a compressed state. Thus, in regions of the compressible material in the non-compressed state one or more such parts may be arranged in separated fashion leading from one said surface towards the other said surface. Indeed, it is possible for such a body to exhibit parts which extend to the first and second surface simultaneously but which are not united either directly or via intermediate parts when the compressible material is in an uncompressed state, but are united when the compressible material is in a compressed state.

One or more of the conductive bodies may comprise an electrically conductive element disposed and orientated within the compressible material to extend substantially in a direction from the first surface to the second surface, such that when the compressible material is in an uncompressed state the separation of the first and second surfaces is sufficient that the conductive element does not extend to the first and second surface simultaneously, whereas when the sensor is subject to the force the compressible material adopts a compressed state having reduced separation between the first and second surfaces such that the conductive element extends to the first and second surfaces simultaneously. In this case the conductive bodies compress by a lesser extent than the compressible material in their immediate vicinity, or substantially not compress at all.

The conductive body or bodies may be of metal or metal coated materials. The conductive bodies may be of conductive polymer materials.

Optionally, at least one of the contact portions is deposited on the first or second surface of the resiliently compressible material.

At least one of the contact portions may be of electrically conductive paint, electrically conductive ink or an electrically conductive polymer.

At least one of the contact portions may comprise conductive textile material.

The sensor may be divided into a plurality of sensor areas and capable of detecting the presence of the force in a said sensor area.

The sensor may be connectable to processing apparatus for receiving and processing signals from said sensor. In this case, the sensor may be connectable to processing apparatus by wireless communication means.

In accordance with another aspect of the present invention there is provided a shoe insole comprising the sensor.

In accordance with another aspect of the present invention there is provided a shoe comprising the insole.

In accordance with another aspect of the present invention there is provided a shoe comprising the insole, the insole being removable.

In accordance with another aspect of the present invention there is provided a shoe comprising the sensor.

In accordance with another aspect of the present invention there is provided a processing apparatus connectable to the sensor, said apparatus configured for receiving and processing signals from said sensor, the apparatus comprising:

input means to receive signals from said sensor;

means for processing the signals in accordance with processing instructions; and output means for providing output data based on the processed signals.

The output data may include a representation of the force exerted by a persons foot on a supporting surface based on signals received from a said sensor interposed between the foot and the supporting surface. The output data may include an indication of distance travelled by a user exerting a force with their foot on a supporting surface, based on signals received from a said sensor interposed between the foot and the supporting surface. The output may be in the form of a visual, audible or tactile representation. The output may include data derived from the distance travelled.

In accordance with another aspect of the present invention there is provided a system comprising the technical features of the processing apparatus and the sensor.

In accordance with another aspect of the present invention there is provided a system comprising the technical features of the processing apparatus and the shoe insole.

In accordance with another aspect of the present invention there is provided a system comprising the technical features of the processing apparatus and the shoe.

These and other aspects of the present invention appear in the appended claims which are incorporated herein by reference and to which the reader is now referred.

The present invention will now be described with reference to the Figures of the accompanying drawings in which.

It should be noted that the drawings are diagrammatic and not drawn to scale. Relative dimensions and proportions of parts of the Figures have been shown exaggerated or reduced in size for the sake of clarity and convenience in the drawings.

Figure 1:
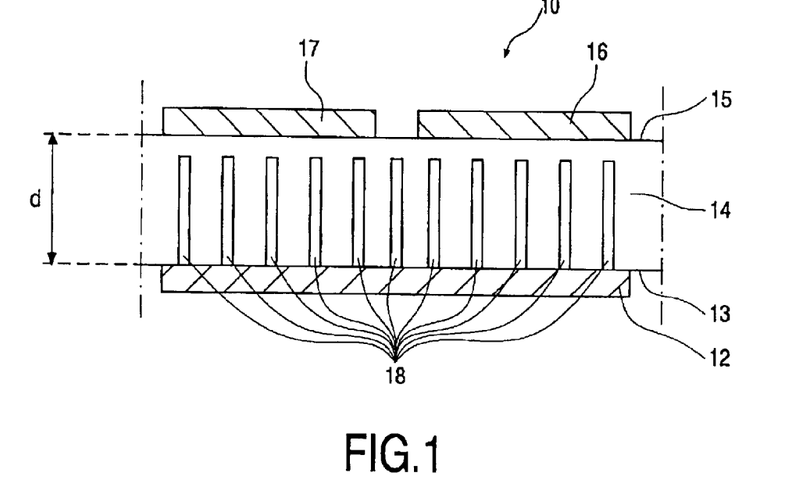
FIG. 1 is a partial cross sectional view of an embodiment of a sensor made in accordance with the present invention shown in a first state.

Referring to FIG. 1, part of an embodiment of the sensor 10 has a lower contact portion in the form of a layer of an electrically conductive textile material 12 adjacent to and in contact with a first surface 13 of resiliently compressible material in the form of elastomeric layer 14. The elastomeric material of layer 14 is capable of yielding-on the application of force to exhibit elastic deformation. The elastomeric layer 14 has a second surface 15 substantially parallel to its first surface 13. Adjacent to and in contact with the elastomeric layer second surface 15 is a first upper contact portion 16 in the form of an electrically conductive textile material. Also adjacent to and in contact with the elastomeric layer second surface 15 is a second upper contact portion 17 in the form of an electrically conductive textile material. The first upper contact portion 16 and second upper contact portion 17 are separated from each other. The electrically conductive material of the lower and upper contact portions is formed of "nylon 66" woven to form a rip-stop fabric and which is electrolessly plated with copper, although versions coated with silver or nickel are also available. This electrolessly plated fabric is commercially available from Shieldex.

The resiliently compressible elastomeric layer 14 is generally of an electrically insulating elastomer but contains a number of electrically conductive bodies in the form of metal filaments 18 which extend substantially in their lengthways direction within the elastomeric material from the first elastomeric layer surface 13 towards the second elastomeric layer surface 15, that is substantially across the thickness of the elastomeric layer 14. When the elastomeric material is in an uncompressed state, the distance between the first and second surface 13 and 15 respectively, denoted 'd' in FIG. 1, is greater than the length of the metal filaments 18. Consequently, when the elastomeric material is in an uncompressed condition the electrically conductive filaments are of insufficient length to extend to the second surface while simultaneously maintaining contact with the first surface 13. However, with reference to FIG. 2, application of force denoted 'F' in the direction shown so as urge the elastomeric layer second surface 15 towards the elastomeric layer first surface 13 causes the elastomeric layer 14 of resiliently compressible material to yield resulting in a reduction in the separation between the first surface 15 and second surface 13. By application of sufficient force 'F' the separation between the first surface 13 and second surface 15 of elastomeric layer 14 is reducible so that it is equivalent to or even less than the length of the metal filaments 18. In this condition the metal filaments 18 are now of a sufficient length that they are able to extend from the first surface 13 of the elastomeric layer to the second surface 15 of the elastomeric layer simultaneously and therefore provide a path of low electrical resistance through the elastomeric layer 14 between the first and second surface 13 and 15 respectively in the locality of reduced elastomeric layer thickness. Thus, the electrical resistance between the first and second surface 13, 15 respectively of the elastomeric layer is reduced in the locality of applied compressive force.

Figure 2:
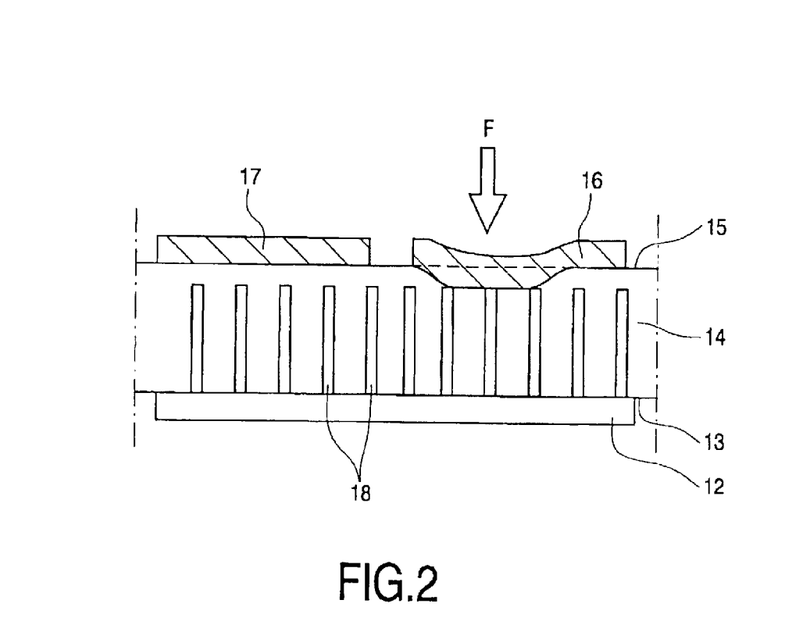
FIG. 2 is a partial cross sectional view of the sensor of FIG. 1 shown in a second state.

In the arrangement of FIGS. 1 and 2, the force F is applied to the elastomeric layer 14 via interposed electrically conductive first upper contact portion 16. As illustrated, when force F is applied to first upper contact portion 16, the thickness of elastomeric layer 14 between first upper contact portion 16 and lower contact portion 12 is reduced until the metal filaments 18 extend to and make electrical contact with the first 13 and second 15 surface of elastomeric layer 14 in the locality of compression and thus provide electrical continuity between adjacent lower contact portion 12 and adjacent first upper contact portion 16. Removal of the applied force 'F' allows elastomeric layer 14 to revert to its uncompressed (thicker) state in which the metal filaments 18 are of insufficient length to extend to the first 13 and second 15 surface of elastomeric layer 14 simultaneously and therefore do not provide electrical continuity therebetween. Thus, no electrical continuity is provided between adjacent lower contact portion 12 and adjacent first upper contact portion 16.

It will be appreciated that the above description is one of an electrical switch in a normally 'open' position but adopting a 'closed' position in the locality of a force causing compression of the elastomeric layer 14.

The elastomeric layer 14 used in the embodiment is a metal loaded elastomer sold as an electromagnetic shielding component by Warth International, East Grinstead, Sussex, England (http://www.warth.co.uk—viewed 5th Nov. 2001) product type SA8, NK2 or SG8. These products are of elastomer loaded with nickel, silver or silver plated aluminium.

The orientation and arrangement of the metal filaments 18 is such that they do not generally come into electrical contact with each other and do not provide for electrical conduction within the layer 14 in any direction except in that direction across the thickness of the layer 14 between surface 13 and 15. Thus electrical continuity is only provided by the metal filaments 18 between surfaces 13 and 15 in the locality of compression of layer 14 and not elsewhere. This means that it is possible to provide a plurality of switches each using a different region of the same elastomeric layer 14. This is illustrated in FIGS. 1 and 2 where a first switch is comprised of lower contact portion 12, elastomeric layer 14 and first contact portion 16, the operation of which has already been described above. A second switch is provided in the form of lower contact portion 12, elastomeric layer 14 and second upper contact portion 17 which operates in the same manner as the first switch. Thus in the case of the second switch, a force F is applied to upper contact portion 17 in the direction of lower contact portion 12 causing compression of interposed elastomeric layer 14 in the locality between contact portions 12 and 17. The reduced thickness of layer 14 allows electrical continuity between contact portions 12 and 17 by virtue of metal filaments 18 extending across the thickness of the elastomeric layer 14.

Because the electrically conductive portions 12, 15 and 17 are of a fabric material they may be stitched using a needle and thread in a manner commonplace in the garment or shoe construction industry. Furthermore, the elastomeric layer 14 is of a material that is penetrable by a needle allowing the conductive portions 12, 15, 17 to be fastened to the elastomeric layer by a sewing process.

One or more of the electrically conductive portions 12, 15 and 17 may be provided in the form of a conductive paint or ink, deposited on the elastomeric layer by appropriate methods, such as by printing, painting, or other deposition techniques.

In the interest of making electrical connection to one or more of the electrically conductive portions, there may be provided on the elastomeric layer (or separate component) electrically conductive tracking extending from the electrically conductive portions to a region convenient for establishing an electrical connection with other components. Thus the electrical connection to other components may be established on the elastomeric layer (or separate component) in a region that is convenient and/or is not subject to compressive forces.

One or more of the electrically conductive portions 12, 15 or 17 may be provided on a separate component, such as a flexible membrane. In this case the portions may be provided on the membrane in the form of conductive metal sheet, conductive ink or paint. The membrane may include conductive tracking for making electrical connection with each of the electrically conductive portions.

Figure 3:
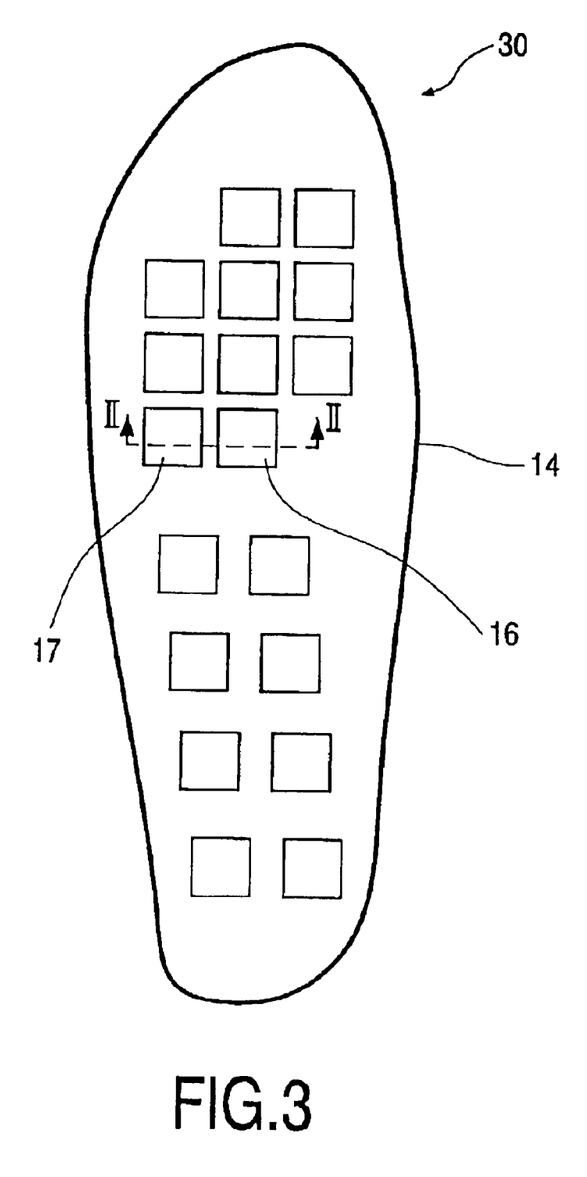
FIG. 3 is a plan view showing the embodiment of the sensor.

A sensor in the form of a shoe insole 30 is shown in FIG. 3 comprising a plurality of sensor portions distributed over the area of the insole, each sensor portion comprising a switch as described above with reference to FIGS. 1 and 2. The first and second upper contact portions 16 and 17 of those switches are shown in FIG. 3 and a total of eighteen upper contact portions, hence switches, are provided. The lower contact portion 12 is common to each switch. In use, a persons foot exerts downward pressure on the insole at particular areas causing operation of the appropriate switches. By connecting each of these sensor areas to processing apparatus the opening and closing of each switch can be monitored to establish which parts of a persons foot exert a pressure on the ground and during which times.

Figure 4:
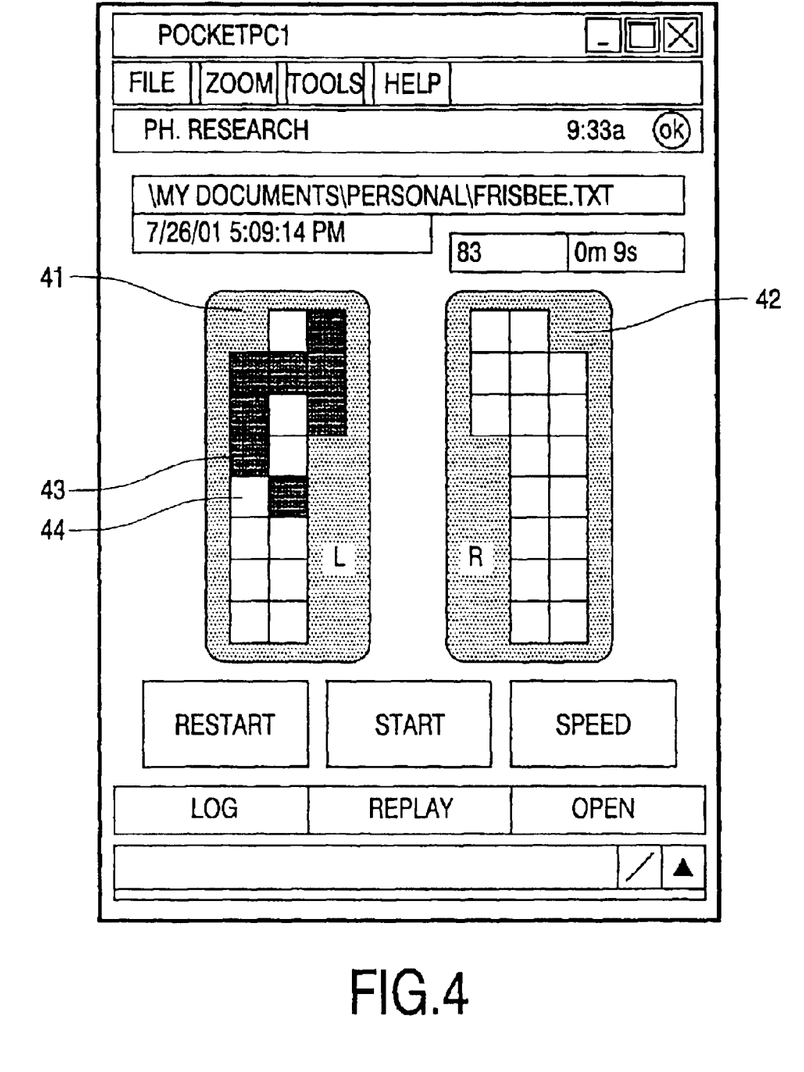
FIG. 4 is a representation of an image on a display screen of a device for displaying information about the sensor status.

In one prototype arrangement, two insoles each having eighteen sensor areas (hence switches) were connected to a detector based on a circuit using a PIC (PIC16C76). Each sensor area (switch) formed part of a potential divider, the output of which was provided to the detector input. The detector monitors each sensor area (switch) at a predetermined frequency to generate a serial output signal representative of switch condition which is conveyed via an RS-232 serial connection to a portable processing device, in this case a Compaq iPAQ running software applications written using Embedded Visual Basic 3.0. One software application generated a graphical representation of the insoles showing the relative locations of the sensor areas with each sensor area representation changing in appearance to indicate whether the switch associated with the sensor was open or closed. This allows for a real-time representation of which sensor areas are subjected to pressure or by storing information received from the detector the sequence of sensor area loading may be 'played back' at will and analysed at a speed chosen by an operator. Such representation is illustrated in FIG. 4 with a representation 41 of the sensor corresponding to the left foot and another representation 42 of the sensor corresponding to the right foot. At a given time, sensor portions which are experiencing a force sufficient to compress the sensor are indicated as a shaded sensor 43 while those portions which are not experiencing a force sufficient to compress the sensor are indicated as unshaded portions 44. Sensor status may be displayed as a function of time, either as a real-time representation or by recalling a stored sensor data file for subsequent analysis.

It will be apparent to a person skilled in the art that other sensor representations are possible as are variations in the sensor area scanning frequency, number of sensor areas, size of each sensor area and location of each sensor area.

In an alternative sensor arrangement, a membrane may be placed on top of the elastomeric material 14 with prearranged contact areas each corresponding to a sensor area. The number of contact areas may be large, for example in the order of a few hundred, with each contact area being tested periodically for electrical continuity with the lower contact 12 via the elastomeric material 14 using appropriate scanning techniques.

Figure 5:
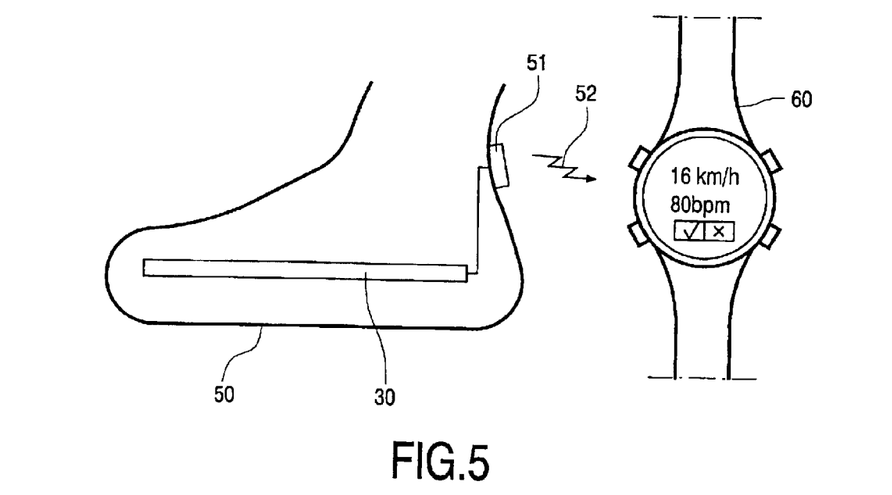
FIG. 5 is an illustration of a shoe incorporating the sensor and a wrist worn device for receiving and processing signals received from the sensor and presenting information to a user.

Referring to FIG. 5, the insole 30 is shown in a running shoe 50. The sensor insole may be a fixed component of the shoe or removable from the shoe for use in another shoe. Alternatively, the sensor insole 30 may be replaced with another sensor insole in the event that the sensor insoles become defective through wear. The sensor insole may also be provided as an accessory for known running shoes allowing a user to adopt the use of such sensor insole equipment at a different time to acquiring the running shoe. A variety of sensor insoles may be provided each being tailored in sensing characteristics to be more appropriate to use in particular sporting activities where, for example, the ideal force required to close a switch of the sensor will be different in walking, running or jumping. Furthermore, shoe sensor insoles may be tailored for use by people of different weight ranges.

The shoe sensor may be provided as an integral part of a shoe in a form other than the insole, for example disposed in the sole of the shoe or as a number of separate distributed sensor components in the heel, arch or front of the shoe.

A system for utilising information obtained from the shoe sensor includes connecting the shoe sensor to a wireless communicator 51 located on the shoe, the wireless communicator serving to communicate information relating to the state of the shoe sensor areas to a wrist worn processing device 60. Communication from the shoe wireless communicator 51 to the processing device 60 is denoted by reference 52 and may be performed by any suitable radio communication protocol, including the so-called 'Bluetooth' communication protocol. The processing device uses information received from the wireless communicator 51 to provide a user with information relating to his physical activity based on forces experienced by the shoe sensor due to the user exerting a force on the ground. By taking into account a users stride length, such information can include the estimated distance travelled, and other information based on calculations of such an estimate, such as average speed. The information may be presented to a user visually, using a display screen or indicator light, audibly in the form of tones or synthesised speech or as a tactile signal, where the watch vibrates. Such information can be presented to the user on the occurrence of particular events, for example when a user has been performing for a particular time or has travelled a particular distance.

The processing device may receive and process information from other sensors, with the option of combining information from more than one sensor to perform analysis of the users activity. Such information includes that relating to limb movement as may be provided by an accelerometer of a pedometer, vertical motion (accelerometer), heart rate and user respiration patterns. The combination of such information may be used to facilitate a wider variety of data analysis options and/or to enhance the accuracy of estimated user activity by combining measurements of more than one sensor. One specific example would be the improvement of data derived from a pedometer tied to the laces of a running shoe by virtue of being able to determine using the shoe sensor when the foot is on the ground and at which moments different areas of the foot sole are on the ground.

The sensor and apparatus may also be used in the process of gait analysis and gait coaching. Information on a users gait can be useful in improving efficiency and skill in their activity of choice and can also be instrumental in injury prevention. In particular the sensor is able to establish those parts of a wearers foot that contact the ground and the sequence in which those parts exert a pressure on the ground. Such data offers an insight into the so-called 'pronation' of a user, and knowledge of whether a person exhibits over pronation, under pronation or neutral pronation can be valuable in their training and selection of footwear. Information on a persons gait and pronation can also be used to improve the accuracy of other equipment, such as equipment which provides data based on measurements derived from an accelerometer based pedometer.

Figure 6:
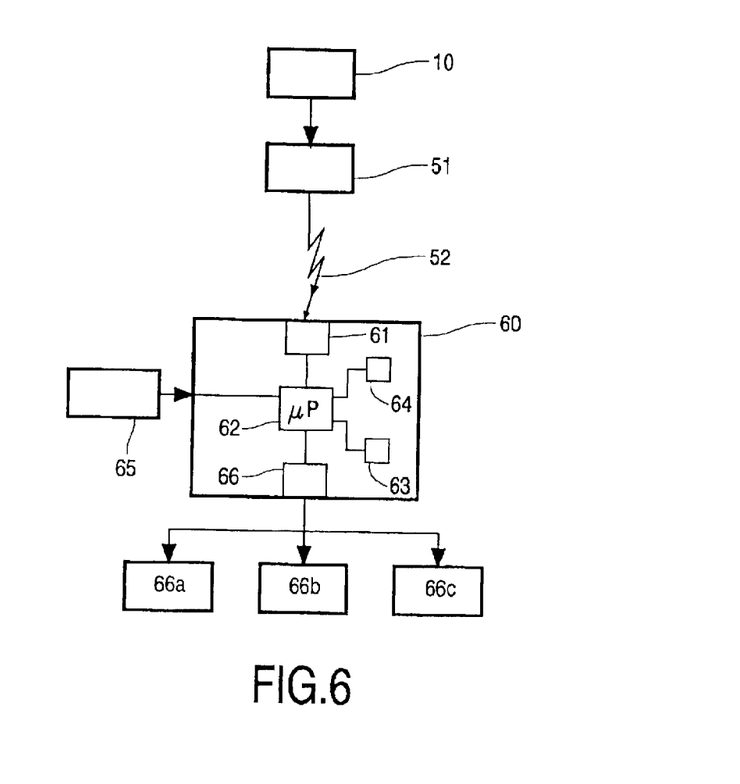
FIG. 6 is a schematic representation of processing apparatus connectable to the sensor.

A representation of the component parts of a system of the present invention is shown in FIG. 6 which includes a shoe sensor 10, of which there may be one for each foot, a wireless transmitter 51 from each shoe sensor, and processing apparatus 60. Processing apparatus includes an input 61, microprocessor 62, storage 63, processing instructions 64, user input interface 65 and output 66. Output 66 is provided for presentation on a display screen 66a, delivery through an audio transducer 66b or as a trigger for tactile signal generator 66c. In an alternative arrangement signals from the sensor may be stored in storage means for analysis at a later time, for example by storage provided in the wireless transmitter 51 or by processing apparatus 60, allowing connection to other processing and analysis equipment, such as a personal computer, which may provide more extensive analysis capabilities.

Elements of the processing apparatus may be incorporated in different component parts as will be appreciated by the person skilled in the art and the representation of particular functional elements being associated with certain component parts is not to be interpreted as a limitation to the scope of the present invention.

Figure 7:
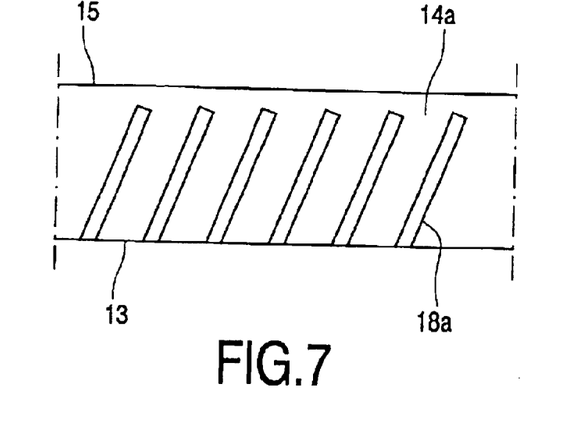
FIG. 7 is a partial cross sectional view of an alternative material for use in a sensor of the present invention.
Figure 8:
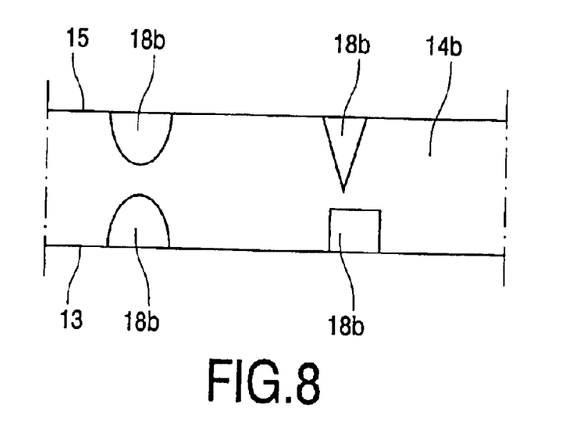
FIG. 8 is a partial cross sectional view representing other alternative materials for use in a sensor of the present invention.

Aspects of the sensor may be altered while remaining within the scope of the present invention, an example being a variant of the elastomeric layer shown in FIG. 7 as elastomeric layer 14a having metal filaments 18a which are not substantially orthogonal to the elastomeric layer surfaces 13 and 15 but instead slanting with respect to that orthogonal. In FIG. 8 the metal filaments 18 or 18a are replaced with conductive bodies 18b each having one of a variety of suitable profiles, three of which are shown. Each body may be arranged to provide electrical continuity from the first surface 13 to the second surface 15 of the elastomeric material in the vicinity of compression of the elastomeric material 14. Alternatively, and as shown in FIG. 8, each electrically conductive body 18b may rely on being brought into contact with one or more electrically conductive body 18b in the vicinity of compression of the elastomeric layer 14b in order to unite and establish a link from one surface 13 to the other surface 15 of the elastomeric layer 14b.

Figure 9:
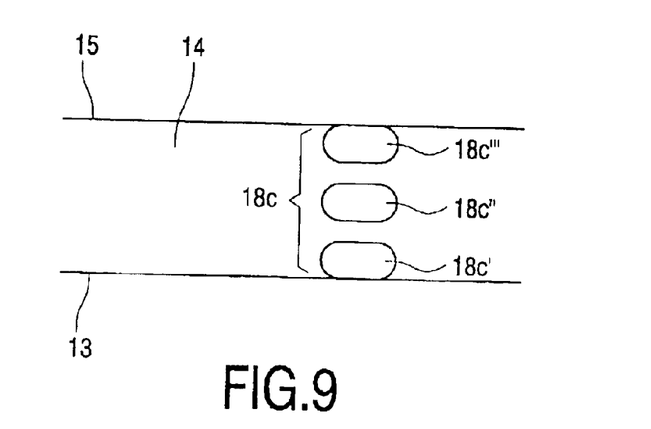
FIG. 9 is a partial cross sectional view of an alternative material for use in a sensor of the present invention.

With reference to FIG. 9, each electrically conductive body 18c may consist of more than one part 18c', 18c'', 18c''' arranged to unite and collectively extend to the first 13 and second 15 surface simultaneously when the material adopts a compressed state. Thus, in regions of the compressible layer 14 in the non-compressed state one or more such parts may be arranged in separated fashion, as shown in FIG. 9, leading from one surface 13 towards the other surface 15. Indeed, it is possible for such a body to exhibit parts which extend to the first 13 and second 15 surface simultaneously but which are not united either directly or via intermediate parts when the compressible material is in an uncompressed state, but are united when the compressible material is in a compressed state.

Optionally, by providing conductive tracking leading from electrically conductive portions of the sensor to a peripheral region of a shoe sole sensor or sensor insole, such an arrangement allows electrical connections to be made near the periphery of the sensor device overall rather than in the vicinity of each individual sensor region which can improve ease of manufacture and implementation in a shoe or insole and potentially offers improved reliability.

Without limitation to the above mentioned embodiment or variations, different regions of the foot pressure sensor may incorporate a different specification of elastomeric layer so that particular areas of the sensor require more or less force to be applied in order to cause the same amount of compression of the elastomeric layer. Some regions of the foot pressure sensor may have a higher density of sensor portions for a given area of sensor than in other areas of the sensor. Increased density may be obtained by having smaller sensor portions. Increased density of sensor regions makes it possible to have a more specific indication of which areas of the sensor are subject to a force.

In general, the conductive bodies, whether or not in the form of filaments, compress by a lesser extent than the compressible material in their immediate vicinity, otherwise the conductive bodies do not compress substantially at all.

The elastomeric material is generally understood to be an electrical insulator although it will be appreciated by the person skilled in the art that providing that its conductivity is generally less than that of the electrically conductive bodies then in principle sensor operation should be possible.

Further, the skilled person will appreciate that particular arrangements of row and column addressing techniques applied to the sensors and appropriate interface circuitry may be employed to establish if a sensor switch (sensor portion) is electrically open or closed.

From reading the present disclosure, other modifications will be apparent to persons skilled in the art. Such modifications may involve other features which are already known in the design, manufacture and use of shoe sensors, processing apparatus suitable for handling information received from such sensors, shoes or insoles suitable for accommodating such sensors, sports equipment, sports training equipment and applications thereof and which may be used instead of or in addition to features already described herein.

What is claimed is:

1. A sensor for detecting the presence of a force exerted by a person's foot on a supporting surface, said sensor arranged to be interposed between the foot and the supporting surface and therefore subjected to the force, in response to which force the sensor exhibits a change in an electrical characteristic, said sensor comprising:

a resilient compressible material having a first surface and a second surface and at least partially accommodating one or more integral electrically conductive body or bodies, shaped and orientated within the material such that when the compressible material is in an uncompressed state the separation of the first and second surfaces is sufficient that the conductive body or bodies do not extend to span the first and second surface simultaneously, whereas when the sensor is subject to the force the compressible material adopts a compressed state having reduced separation between the first and second surfaces such that the conductive body or bodies extend to and span the first and second surfaces simultaneously; and substantially flat contact portions adjacent each of the first and second surface for making electrical connection with the electrically conductive body or bodies when they extend to the or each first and second surface.

2. A sensor in accordance with claim 1 wherein one or more of the conductive bodies may consist of more than one part each arranged to unite and collectively extend to the first and second surface simultaneously when the material adopts a compressed state.

3. A sensor in accordance with claim 1 wherein one or more of the conductive bodies comprises an electrically conductive element disposed and orientated within the material to extend substantially in a direction from the first surface to the second surface.

4. A sensor in accordance with claim 1, wherein the conductive body or bodies are of metal or metal coated materials.

5. A sensor in accordance with claim 1 wherein at least one of the contact portions is deposited on the first or second surface of the resiliently compressible material.

6. A sensor in accordance with claim 5 wherein at least one of the contact portions is of electrically conductive paint, electrically conductive ink or an electrically conductive polymer.

7. A sensor in accordance with claim 1 wherein at least one of the contact portions comprises conductive textile material.

8. A sensor in accordance with claim 1, said sensor being divided into a plurality of sensor areas and capable of detecting the presence of the force in a said sensor area.

9. A sensor in accordance with claim 1 connectable to processing apparatus for receiving and processing signals from said sensor.

10. A sensor in accordance with claim 9 wherein the sensor is connectable to processing apparatus by wireless communication means.

11. A shoe insole comprising the sensor of claim 1.

12. A shoe comprising the sensor of claim 1.

13. A shoe comprising the insole of claim 11.

14. A shoe comprising the insole of claim 11, wherein the insole is removable.

15. A processing apparatus connectable to the sensor of claim 1 said apparatus configured for receiving and processing signals from said sensor, the apparatus comprising:

input means to receive signals from said sensor;

means for processing the signals in accordance with processing instructions; and output means for providing output data based on the processed signals.

16. The processing apparatus in accordance with claim 15, wherein said output data includes a representation of the force exerted by a persons foot on a supporting surface based on signals received from a said sensor interposed between the foot and the supporting surface.

17. The processing apparatus in accordance with claim 15, wherein said output data includes an indication of distance travelled by a user exerting a force with their foot on a supporting surface, based on signals received from a said sensor interposed between the foot and the supporting surface.

18. The processing apparatus of claim 17 wherein said output data includes data derived from the distance travelled.

19. The processing apparatus of claim 15, wherein the output data is in the form of a visual, audible or tactile representation.

20. A system comprising the technical features of the processing apparatus of claim 15 and the sensor for detecting the presence of a force exerted by a persons foot on a supporting surface, said sensor arranged to be interposed between the foot and the supporting surface and therefore subjected to the force, in response to which force the sensor exhibits a change in an electrical characteristic, said sensor comprising:

a resilient compressible material exhibiting a first surface and a second surface and at least partially accommodating one or more electrically conductive body shaped and orientated within the material such that when the compressible material is in an uncompressed state the separation of the first and second surfaces is sufficient that the conductive body or bodies do not extend to span the first and second surface simultaneously, whereas when the sensor is subject to the force the compressible material adopts a compressed state having reduced separation between the first and second surfaces such that the conductive body or bodies extend to and span the first and second surfaces simultaneously; and contact portions adjacent each of the first and second surface for making electrical connection with the electrically conductive body or bodies when they extend to the or each first and second surface.

* * * * *